(12) United States Patent
Lee

(10) Patent No.: US 7,456,112 B2
(45) Date of Patent: Nov. 25, 2008

(54) METHOD OF FABRICATING MICRO-NEEDLE ARRAY

(75) Inventor: Chang-seung Lee, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 203 days.

(21) Appl. No.: 11/327,463

(22) Filed: Jan. 9, 2006

(65) Prior Publication Data

US 2006/0172541 A1 Aug. 3, 2006

(30) Foreign Application Priority Data

Feb. 3, 2005 (KR) .................... 10-2005-0009916

(51) Int. Cl.
*H01L 21/302* (2006.01)
(52) U.S. Cl. ................ 438/735; 257/E21.273
(58) Field of Classification Search .......... 438/735, 438/737, 738; 257/E21.273
See application file for complete search history.

(56) References Cited

U.S. PATENT DOCUMENTS

| 6,503,231 | B1 | 1/2003 | Prausnitz et al. | |
|---|---|---|---|---|
| 2005/0011858 | A1* | 1/2005 | Kuo et al. | 216/17 |
| 2006/0015061 | A1* | 1/2006 | Kuo et al. | 604/47 |

\* cited by examiner

*Primary Examiner*—Lex Malsawma
(74) *Attorney, Agent, or Firm*—Sughrue Mion, PLLC

(57) ABSTRACT

A method of fabricating a micro-needle array is provided. The method of fabricating a micro-needle array having a substrate having a first surface and a second surface spaced in a predetermined interval apart from the first surface, includes patterning on the first surface, thereby forming a shape of micro-needle bodies. Further, micro-passageways are formed that penetrate the first surface of the substrate from the second surface by a porous silicon process, and integrates the micro-passageways, thereby forming the bodies and channels of micro-needles.

16 Claims, 11 Drawing Sheets

METHOD OF FABRICATING MICRO-NEEDLE ARRAY

CROSS-REFERENCE TO RELATED APPLICATIONS

This application claims priority from Korean Patent Application No. 10-2005-0009916, filed Feb. 3, 2005, the entire content of which is incorporated herein by reference.

BACKGROUND OF THE INVENTION

1. Field of the Invention

The present invention relates to a method of fabricating a micro-needle array, and more particularly, to fabricating a micro-needle array for obtaining and injecting micro-fluidic samples by using micro-machining fabrication technologies.

2. Description of the Related Art

Recently, with advancements of the micro-electro mechanical system (MEMS) and micro-machining technologies, more attention is paid to micro-needles.

A micro-needle has a micrometer-level channel diameter, and is used in a variety of fields. For example, a micro-needle is used as an accurate cell injection/extraction needle in the field of cell-biology, or used as an injection/extraction head for chemicals or solutions in chemicals delivery systems or in micro-chemicals factories. In addition, since a small-sized needle reduces inconvenience and pain associated with injections, micro-needles are advantageous in injecting medication into patients.

FIGS. 1A to 1G show a method of fabricating a glass or a silicon micro-needle through isotropic etching. As shown in FIGS. 1A to 1G, the conventional micro-needle array fabrication method, first, an isotropic etching mask 11 is vapor-deposited on a glass or a silicon substrate 10, and a hole pattern 12 is formed through a lithography process. Next, a channel 13 is formed in the glass or silicon substrate 10 through Deep Reactive Ion Etching (DRIE), and the surface of the substrate 10 is coated so that the channel is not etched. Then, a shape 15 is formed for isotropic etching on the front surface, a pointed tip 16 like a needle is formed through BHF etching, HF etching, or HNA etching, and, finally, the metal 11 used for the mask is removed, thereby fabricating a micro-needle 17. FIG. 2 shows an image of micro-needles fabricated according to the above method.

FIGS. 3A to 3E show a micro-needle fabrication method using silicon. As shown in FIGS. 3A to 3E, in the micro-needle fabrication method, first, a trench 21 is formed on silicon 20 through DRIE, and a channel 22 is formed on the opposite side in the same way. Next, the whole silicon 23 is coated in order to protect structure from silicon etching solution. Subsequently, the coating mask on top of the silicon is removed, and a slant surface 24 is formed by using anisotropic etching. Finally, the slant surface 24 is etched by an appropriate depth, and the coating 23 is removed, thereby completing a micro-needle 25. FIG. 4 shows an image of a micro-needle fabricated according to the above described micro-needle fabrication method.

As above, a conventional micro-needle fabrication method uses DRIE to form micro-needle channels in the substrate, but DRIE as above has a limitation with respect to a ratio of channel diameter to channel length, i.e. an aspect ratio. A micro-needle is required in itself to have a diameter less than tens of μm, but limitations exist in fabricating a micro-needle that has such a short diameter and a long channel due to the characteristics of current semiconductor equipment. Generally, the maximum aspect ratio of a micro channel that can be fabricated through DRIE is approximately 1:10. However, a micro-channel is required to be hundreds of μm long for its use, but it is difficult to form a channel having a diameter less than 10 μm and a length of hundreds of μm with conventional DRIE.

In addition, the conventional method is incapable of forming a silicon oxide needle having a high aspect ratio and a channel which is surrounded with a silicon oxide body.

SUMMARY OF THE INVENTION

The present invention has been developed in order to solve the above drawbacks and other problems associated with the conventional arrangement. An aspect of the present invention provides a method of fabricating a micro-needle array with a high aspect ratio and a silicon or silicon oxide body.

The foregoing and other aspects are substantially realized by providing a method of fabricating a micro-needle array including bodies and channels on a substrate. The substrate has a first surface and a second surface spaced in a predetermined interval apart from the first surface is prepared. Further, a shape of the bodies is formed by patterning the first surface of the substrate. A plurality of micro-passageways that penetrate the first surface of the substrate from the second surface are formed by a porous silicon process. Channels are formed on the substrate by removing walls formed between the plurality of micro-passageways that penetrate the first surface of the substrate from the second surface.

Further, the porous silicon process may be a macro-porous silicon process.

The porous silicon process further includes forming a plurality of notches on predetermined areas of the second surface, and the plurality of micro-passageways are vertically formed corresponding to the plurality of notches.

The predetermined areas where the plural notches are formed become areas other than areas where the bodies are formed. Accordingly, micro-passageways are formed at the areas where the notches are formed, and the walls formed between the plural micro passageways are removed, thereby forming the channels of the micro-needles. Further, bodies are formed at the areas where the notches are not formed.

By doing so, silicon micro-needles may be formed with bodies surrounding the channels that are silicon.

According to another aspect, a method of fabricating a micro-needle array including bodies and channels on a substrate is provided, as follows. The substrate has a first surface and a second surface spaced in a predetermined interval apart from the first surface is prepared. Further, a shape of the bodies is formed by patterning the first surface of the substrate. A plurality of micro-passageways that penetrate the first surface of the substrate from the second surface are formed by a porous silicon process. Passivation layers are formed and grow on the surfaces of the walls formed between the plurality of micro-passageways, thereby forming the bodies. Further, channels are formed by removing portions of the substrate other than the bodies on the substrate.

The predetermined areas where the plurality of notches are formed may be areas where the bodies are formed. Accordingly, micro-passageways are formed on the areas where notches are formed, and the passivation layers grow on the micro-passageways, so the bodies are formed. Further, the portions of the substrate where the notches are not formed is removed through etching to form the channels.

Further, the passivation layer may be silicon oxide ($SiO_2$).

Accordingly, silicon oxide micro-needles are formed with bodies surrounding the channels that are silicon oxide.

BRIEF DESCRIPTION OF THE DRAWINGS

The above and other aspects of the present invention will be more apparent by describing certain exemplary embodiments of the present invention with reference to the accompanying drawings, in which.

DETAILED DESCRIPTION OF THE EXEMPLARY EMBODIMENTS OF THE INVENTION

Hereafter, description will be made on a method of fabricating a micro-needle array according to exemplary embodiments of the present invention with reference to accompanying drawings.

FIGS. 5A to 5H are views for showing a method of fabricating a silicon micro-needle array according to an exemplary embodiment of the present invention.

Figure 1A:
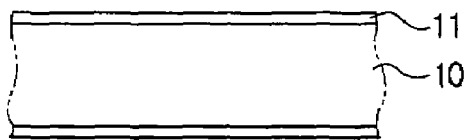
FIGS. 1A to 1G are views for showing a method of fabricating a micro-needle array according to a conventional technology.
Figure 1B:
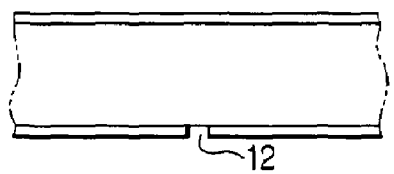
Figure 1C:
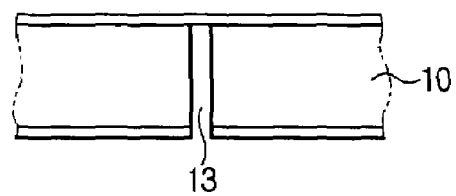
Figure 1D:
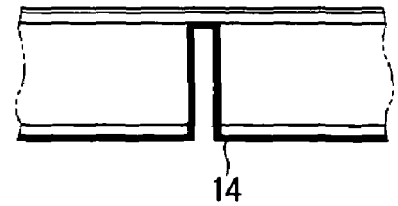
Figure 1E:
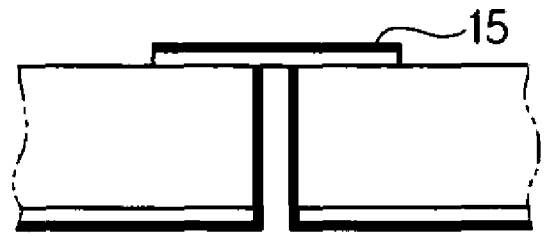
Figure 1F:
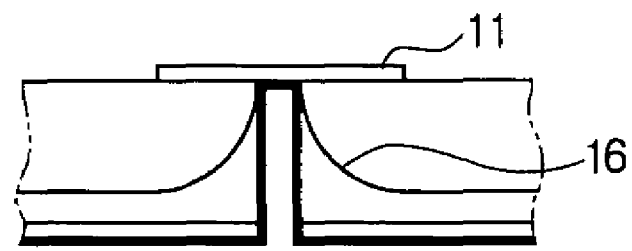
Figure 1G:
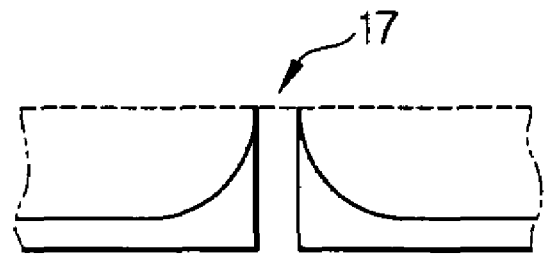
Figure 2:
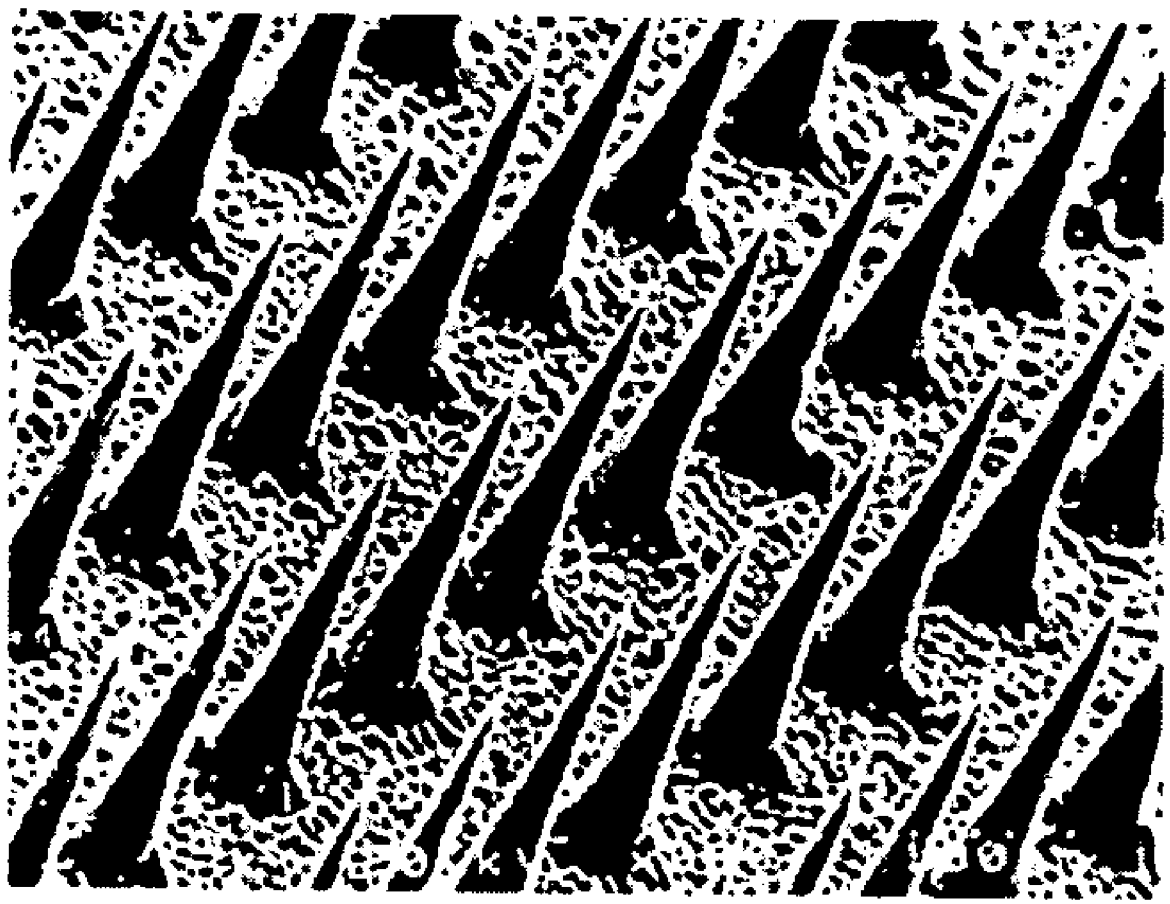
FIG. 2 is a view for showing an image of a micro-needle array fabricated through the of FIGS. 1A to 1G.
Figure 3A:
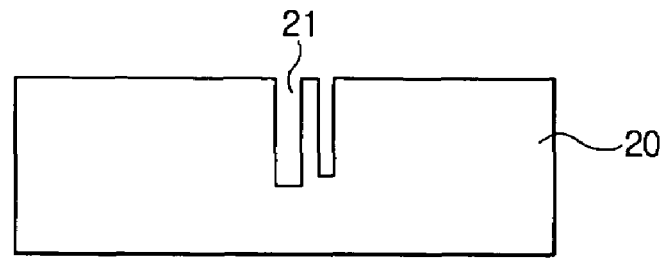
FIGS. 3A to 3E are views for showing a method of fabricating a micro-needle array according to a conventional technology.
Figure 3B:
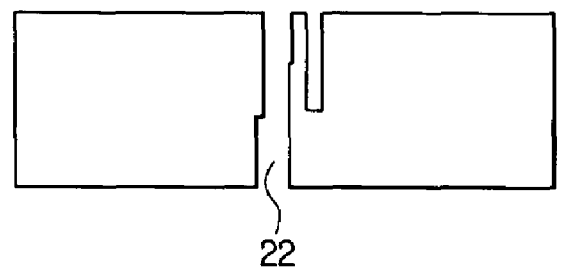
Figure 3C:
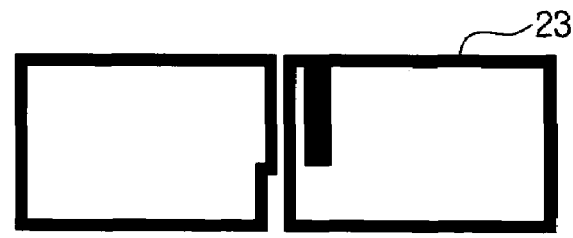
Figure 3D:
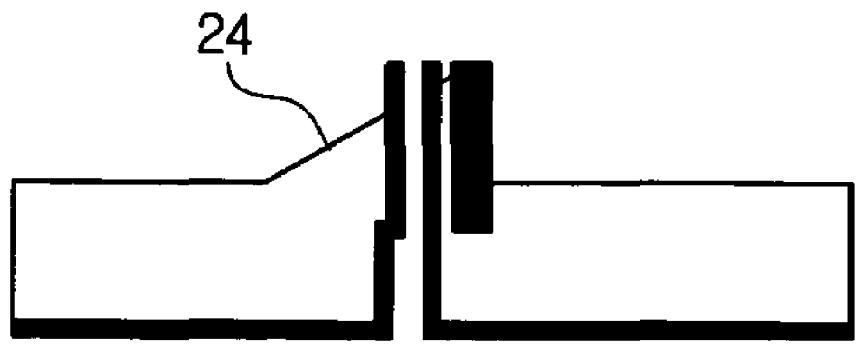
Figure 3E:
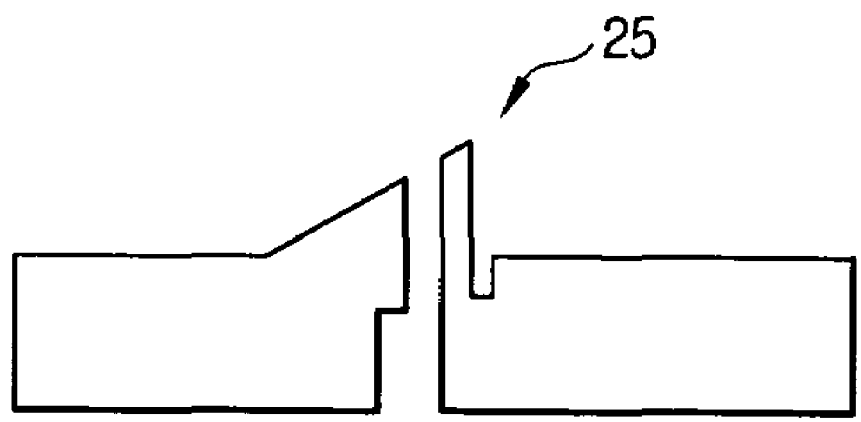
Figure 4:
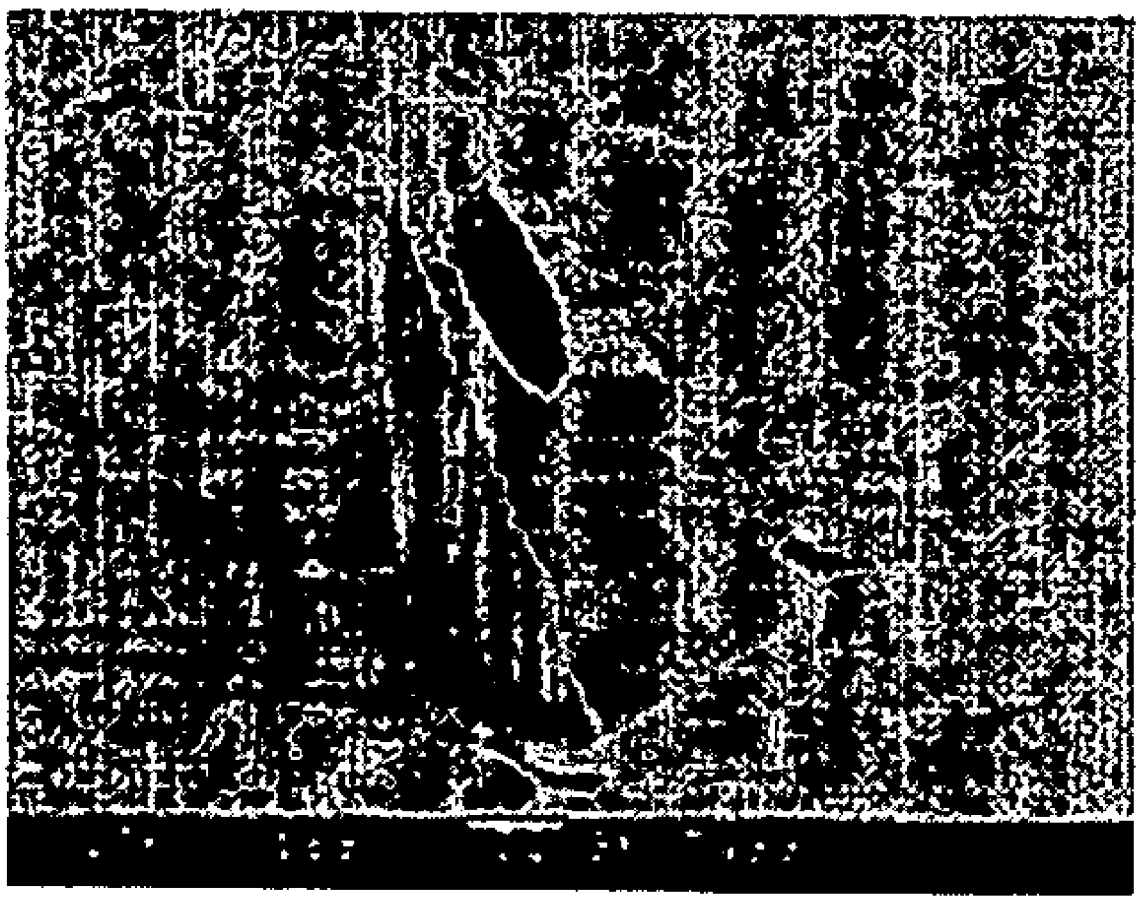
FIG. 4 is a view for showing an image of a micro-needle array fabricated through the method of FIGS. 3A to 3G.
Figure 5A:
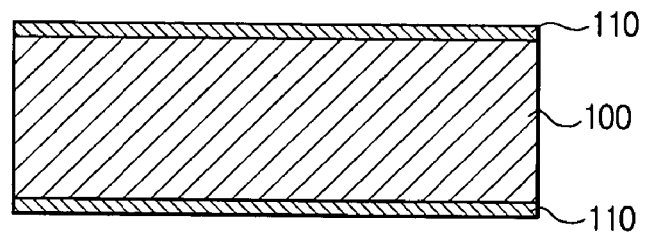
FIGS. 5A to 5H are views for showing a method of fabricating a silicon micro-needle array according to an exemplary embodiment of the present invention.
Figure 5B:
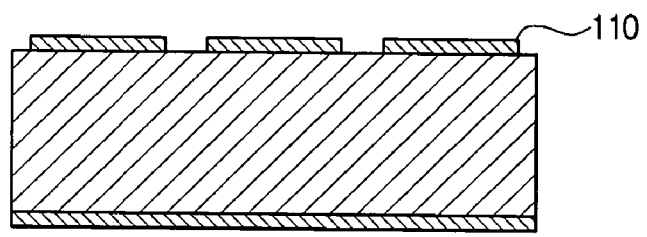

As shown in FIG. 5A, insulation layers 110 are formed on the top and bottom surfaces of a substrate 100 as etching masking layers of the substrate 100. A single-crystal silicon wafer is generally used as the substrate 100. The insulation layers 110 are formed of silicon oxide ($SiO_2$) formed by oxidizing the overall surface of the substrate 100 by the thermal oxidation method, or of nitride layers formed through the Chemical Vapor Deposition (CVD) method Next, as shown in FIG. 5B, patterning is performed so that the insulation layers 110 are divided in a certain shape.

Figure 5C:
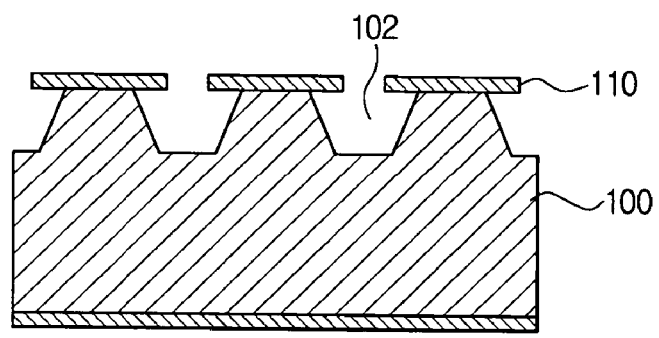
Figure 5D:
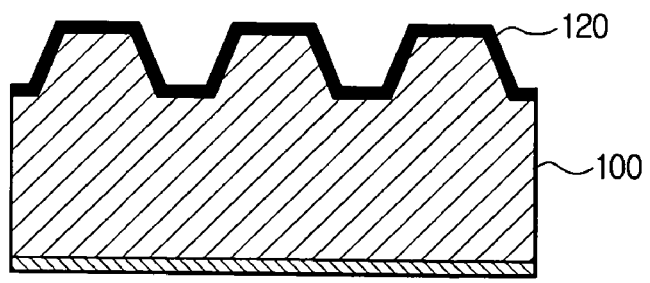

Next, as shown in FIG. 5C, an etching process is performed on the top surface of the substrate 100 except the insulation layer 110, so trenches 102 of a certain thickness are formed. Then, as shown in FIG. 5D, the insulation layers 110 are removed, and a passivation layer 120 is vapor-deposited on the whole top surface of the substrate 100. The passivation layer 120 can be, for example, any of a silicon oxide layer and a silicon nitride layer, which can be vapor-deposited through the low pressure chemical vapor deposition (LPCVD). In addition, instead of low pressure chemical vapor deposition, a biocompatible organic thin film such as a parylene thin film can be used for coating.

Figure 5E:
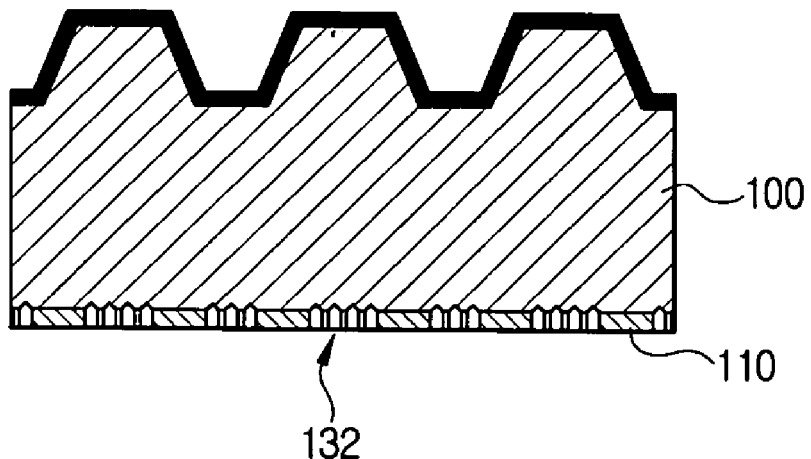

Next, as shown in FIG. 5E, patterning is performed so that plural notches 132 are formed at certain areas of the insulation layer 110 on the bottom surface of the substrate 100. The certain areas where notches are formed refer to the areas other than areas where the bodies 150 (refer to FIG. 5G) of micro-needles, which will be described later, are formed.

Figure 5F:
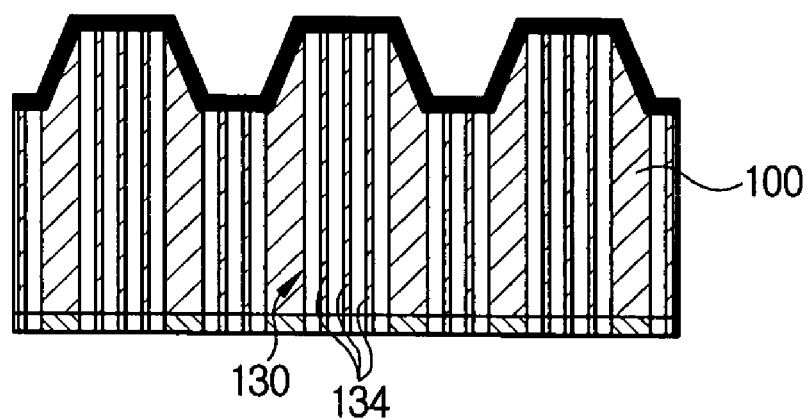
Figure 5G:
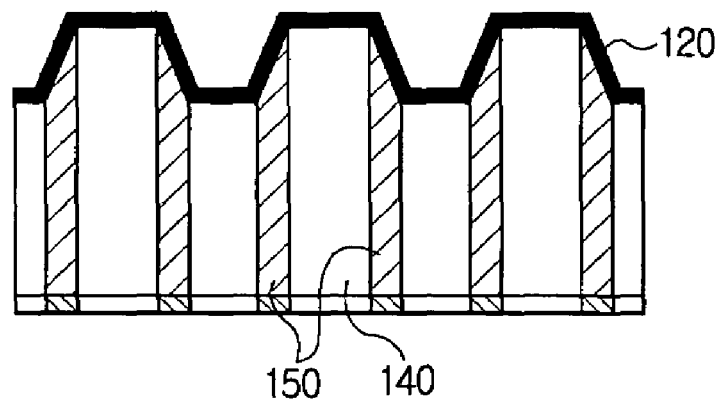

In FIG. 5G, a macro-porous silicon process is performed on the substrate 100 where the notches 132 are formed, and micro-passageways 130 are formed to the top surface from the bottom surface of the substrate 100 where the notches 132 are formed.

The porous silicon process is a type of electrochemical etching, which is low in processing cost and enables a hole or a channel having an extremely high aspect ratio to be obtained. Further the porous silicon process may be classified into nano-porous silicon and macro-porous silicon.

The nano-porous silicon forms nano-sized cavities on the surface of a silicon substrate, which is silicon with the cavities that are connected to one another like a mesh net, and of which chemical and optical characteristics are different. The nano-porous silicon is created on a substrate in a hydrofluoric acid (HF) solution to which electric potential is applied, and the surface of the silicon substrate is minutely etched to be porous. Here, the nano-porous silicon can be formed on the p-type silicon substrate since electronic holes taking part in etching reaction play important roles.

The cavities in the macro-porous silicon are formed on a silicon substrate and are larger than those of the nano-porous silicon. Unlike the nano-porous silicon, the macro-porous silicon can be anisotropically etched in the vertical direction and formed on the n-type silicon. The difference in fabrication processes macro-porous silicon from nano-porous silicon is the creation of electronic holes by exposure to light on the opposite surface of the cavities formed on the silicon substrate. In vertical etching, the number of electronic holes, which are created in the silicon, are maintained at a certain level by controlling the amount of light. Notches are formed in advance on the surface of a silicon substrate for macro-porous silicon fabrication, which enables the vertical etching since electronic holes of positive electric charges are gathered if the charges are concentrated to the notches.

As above, micro-passageways 130 having diameters of 0.05~several μm are formed through the macro-porous silicon process. The diameters of the micro-passageways 130 can be adjusted by controlling the amount of light.

Next, as shown in FIG. 5G, the substrate 100 having micro-passageways 130 formed therein is etched by the tetra methyl ammonium hydroxide (THMA) or hydroxy-nitric-acetic acid (HNA) solution. Thus, the walls 134 between plural micro-passageways 130 are removed, so a channel 140 of a micro-needle is formed as the plural micro-passageways 130 are integrated as shown. The diameter of the channel 140 can be formed to be approximately several μm~several tens of μm. Then, the body 150 of a micro-needle is formed around the channel 140. The length (L) of the body 150 generally corresponds to the thickness of a silicon wafer being the substrate 100, which is approximately 400~500 μm. As above, the present exemplary embodiment can form a channel having a ratio approximately of 1:20 or more than 1:20, as a ratio of diameter to length of a channel 140, i.e. an aspect ratio.

Figure 5H:
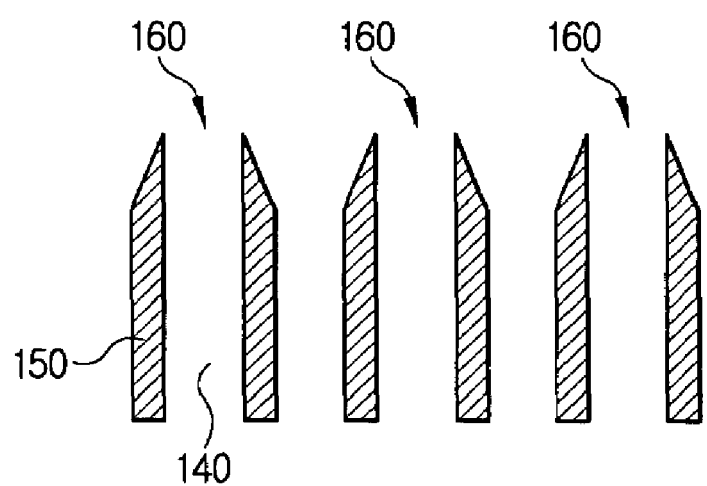

Next, as shown in FIG. 5H, the passivation layer 120 of the bodies 150 is removed, so a silicon micro-needle array formed with plural micro-needles 160 is formed, wherein respective micro-needles have a channel 140 and a silicon body 150.

FIGS. 6A to 6E are views for showing a method of fabricating a silicon oxide needle array according to another exemplary embodiment of the present invention. The previous exemplary embodiment forms the bodies 150 of silicon to surround the micro-needle channels 140, but the present exemplary embodiment forms the bodies 150 of silicon oxide ($SiO_2$).

On the other hand, the body 150 of a micro-needle 160 has the end point formed slanted and pointed in the previous exemplary embodiment, but the end portion of a body has a shape of a parallel-tube such as a cylindrical tube, a rectangular tube, or the like in the present exemplary embodiment. Since it is possible to fabricate the end portion of the body 150 in a tube shape as above through a general mask process, a PR process, and an etching process, so detailed description will not be made on the fabrication method. Further, according to an exemplary embodiment, even a silicon oxide needle can be formed with a body having a pointed end portion.

Figure 6A:
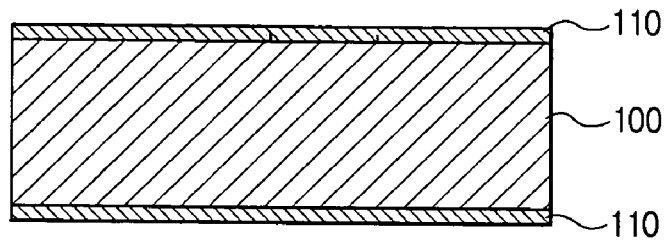
FIGS. 6A to 6E are views for showing a method of fabricating a silicon oxide needle array according to another exemplary embodiment of the present invention.
Figure 6B:
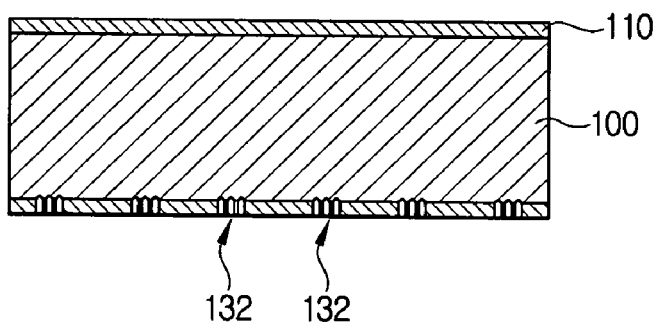
Figure 6C:
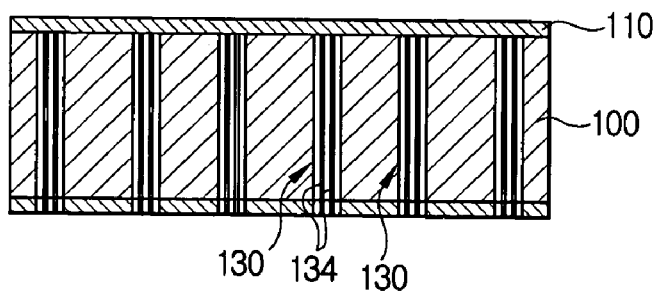

As shown in FIG. 6A, a substrate 100 having insulation layers 110 formed on the top and bottom thereof is prepared. Patterning is performed on the insulation layer 110 of the top surface so that an end portion of a body 150 is formed. The processes of FIGS. 6B and 6C are the same as those of FIGS. 5E and 5F shown in the previous exemplary embodiment. That is, plural notches 132 are formed at certain areas of the bottom surface of the substrate 100, and then micro-passageways 130 are formed to penetrate the substrate 100 through the macro-porous silicon process at the areas where the plural notches 132 are formed. Here, the areas of the notches 132 are the areas where bodies 150 of micro-needles are formed, unlike the previous exemplary embodiment.

Figure 6D:
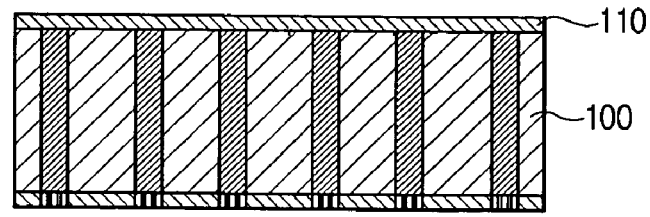

In FIG. 6D, the substrate 100 having the micro-passageways 130 formed thereon is oxidized through the thermal oxidation, so silicon oxide ($SiO_2$) is formed. The silicon oxide grows from the surfaces of walls 134 around the micro-passageways 130 to fill in the plural micro-passageways 130. The silicon oxide grown as above forms the bodies 150 of the micro-needles. Generally, a silicon oxide layer grows in a curve of an exponential function, so that it takes quite a long time for the silicon oxide layer to grow more than a certain thickness, for example, 2~3 μm. Therefore, conventionally, it is very difficult to fabricate the bodies of micro-needles which are formed of silicon oxide. However, the present exemplary embodiment grows the silicon oxide the surfaces of the walls 134 around the micro-passageways 130 having a very small diameter, so the bodies 150 of micro-needles can be formed of silicon oxide.

Figure 6E:
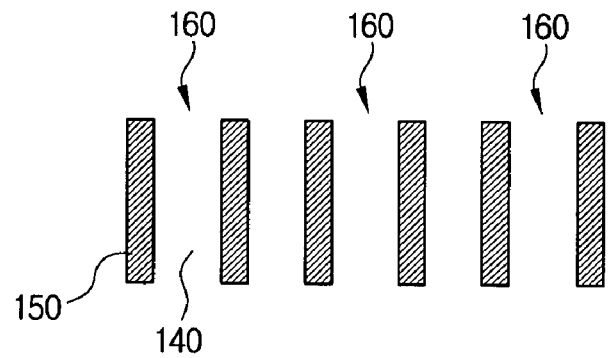

Next, as shown in FIG. 6E, except for the bodies 150, the other portions of the substrate 100 are removed through wet etching. Since the substrate 100 is removed through etching, channels 140 for micro-needles 160 are formed between the bodies 150. By doing so, the present exemplary embodiment forms a silicon oxide micro-needle array formed with plural micro-needles 160 having the channels 140 and the bodies 150 formed of silicon oxide.

Figure 7:
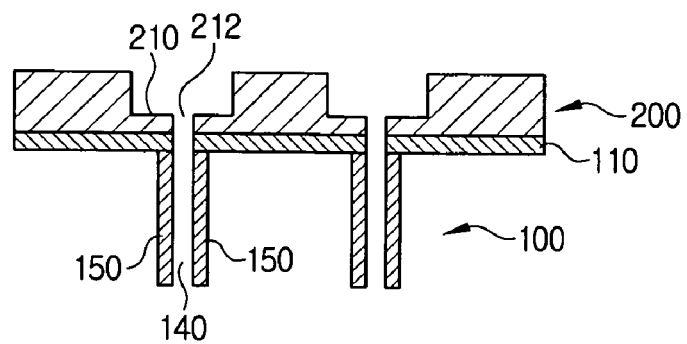
FIG. 7 is a view for showing a micro-syringe array to which a micro-needle array is applied according to an exemplary embodiment of the present invention.

FIG. 7 is a view for showing a micro-syringe array using a micro-needle array according to an exemplary embodiment of the present invention.

As shown in FIG. 7, a first substrate 100 having a micro-needle array formed thereon is bonded with an additional second substrate 200. Even though not shown in here, as in the previous exemplary embodiment, the first substrate 100 is preferably formed with an insulation layer 110 on the surface that is in contact with the second substrate 200. Next, a separate etching process is applied to the second substrate 200 to form trenches 210 having inlets 212, and the silicon direct bonding process is applied to bond the second substrate 200 with the first substrate 100. In addition to the silicon direct bonding, diverse bonding methods may be used to bond the first and second substrates 100 and 200. The inlet 212 of the trench 210 of the second substrate 200 serves as an opening for injecting chemicals or samples.

Next, channels and bodies 150 are formed on the first substrate 100 in accordance with the macro-porous silicon process described for the previous exemplary embodiment, so a micro-needle array is formed. Next, a reactive ion etching process is applied to remove the insulation layer 110 in order for the inlets 212 of the trenches 210 of the second substrate 200 to communicate with the channels 140 of the first substrate 100, so a micro syringe array is finally formed as shown. A micro pump or the like is preferably connected to the trench 210 of the second substrate 200 so as to supply chemicals or samples to the channel 140.

As aforementioned, the micro-needle array fabrication method according to aspects of the present invention can form a micro needle having a very high ratio of the diameter to length of a channel, i.e. a very high ratio of width to height. In addition, the method has an effect capable of implementing a micro-needle having a body of silicon oxide as well as silicon.

The foregoing exemplary embodiments are not to be construed as limiting the present invention. The present teaching can be readily applied to other types of apparatuses. Also, the description of the exemplary embodiments of the present invention is intended to be illustrative, and not to limit the scope of the claims, and many alternatives, modifications, and variations will be apparent to those skilled in the art.

What is claimed is:

1. A method of fabricating a micro-needle array including bodies and channels on a substrate, said substrate having a first surface and a second surface that is spaced apart from the first surface in a predetermined interval, the method comprising:
    forming a shape of the bodies by patterning the first surface of the substrate;
    forming a plurality of micro-passageway groups, each of which comprises a plurality of micro-passageways, that penetrate the first surface of the substrate from the second surface by a porous silicon process, and corresponds to each of the channels; and
    forming each of the channels in the substrate by removing walls formed between the plurality of micro-passageways that constitutes each of the plurality of micro-passageway groups that corresponds to each of the channels.

2. The method as claimed in claim 1, wherein the porous silicon process in the forming the plurality of micro-passageway groups is a macro-porous silicon process.

3. The method as claimed in claim 2, wherein the forming the plurality of micro-passageway groups further includes forming a plurality of notches at predetermined areas of the second surface, wherein the plurality of micro-passageways are vertically formed corresponding to the plurality of notches.

4. The method as claimed in claim 3, wherein, in the forming the plurality of notches, the predetermined areas having the plurality of notches formed thereon are areas other than areas where the bodies are formed.

5. The method as claimed in claim 1, wherein, in the forming the each of the channels by removing the walls, the walls are etched away.

6. The method as claimed in claim 5, wherein the etching away of the walls is performed by tetra methyl ammonium hydroxide (TMAH) or hydroxyl-nitric-acetic acid (HNA) solution.

7. The method as claimed in claim 1, wherein the substrate is a single-crystal silicon wafer.

8. The method as claimed in claim 1, wherein, in the forming the shape of the bodies, end portions of the bodies are formed in any of a sharp shape that tapers outward, a cylindrical tube shape, a rectangular tube shape, and a triangular tube shape.

9. The method as claimed in claim 1, wherein the forming the shape of the bodies includes:

forming an insulation layer on the first surface of the substrate;

patterning the insulation layer that is formed;

forming trenches on the first surface of the substrate by etching;

removing the insulation layer that is patterned; and forming a passivation layer on the first surface of the substrate.

10. A method of fabricating a micro-needle array including bodies and channels on a substrate, the substrate having a first surface and a second surface that is spaced apart from the first surface, the method comprising:

forming a shape of the bodies by patterning the first surface of the substrate;

forming a plurality of micro-passageway groups, each of which comprises a plurality of micro-passageways, that penetrate the first surface of the substrate from the second surface by a porous silicon process, and corresponds to each of the bodies;

forming each of the bodies by forming and growing passivation layers on surfaces of walls formed between the plurality of micro-passageways that constitutes each of the plurality of micro-passageway groups that corresponds to each of the bodies, the surfaces of the walls facing the micro-passageways; and forming the channels between two neighboring bodies by removing portions of the substrate other than the bodies on the substrate.

11. The method as claimed in claim 10, wherein the porous-silicon process in the forming the plurality of micro-passageway groups is a macro-porous silicon process.

12. The method as claimed in claim 11, wherein the forming the plurality of micro-passageway groups further includes forming a plurality of notches on predetermined areas of the second surface, wherein the plurality of micro-passageways are vertically formed corresponding to the plurality of notches.

13. The method as claimed in claim 12, wherein, in the forming the plurality of notches, the predetermined areas having the plurality of notches formed thereon are areas where the bodies are formed.

14. The method as claimed in claim 10, wherein the passivation layer is silicon oxide ($SiO_2$).

15. The method as claimed in claim 10, wherein, in the forming the shape of the bodies, the bodies are shaped in any of a sharp shape having an end portion that tapers outward, a cylindrical tube shape, a rectangular tube shape, and a triangular tube shape.

16. The method as claimed in claim 10, wherein the forming the shape of the bodies includes:

forming an insulation layer on the first surface of the substrate;

patterning the insulation layer that is formed;

forming trenches on the first surface of the substrate through etching;

removing the insulation layer that is patterned; and forming a passivation layer on the first surface of the substrate.

* * * * *